March 21, 1967 E. S. BOERNER Plant Pat. 2,729
ROSE PLANT
Filed April 14, 1966
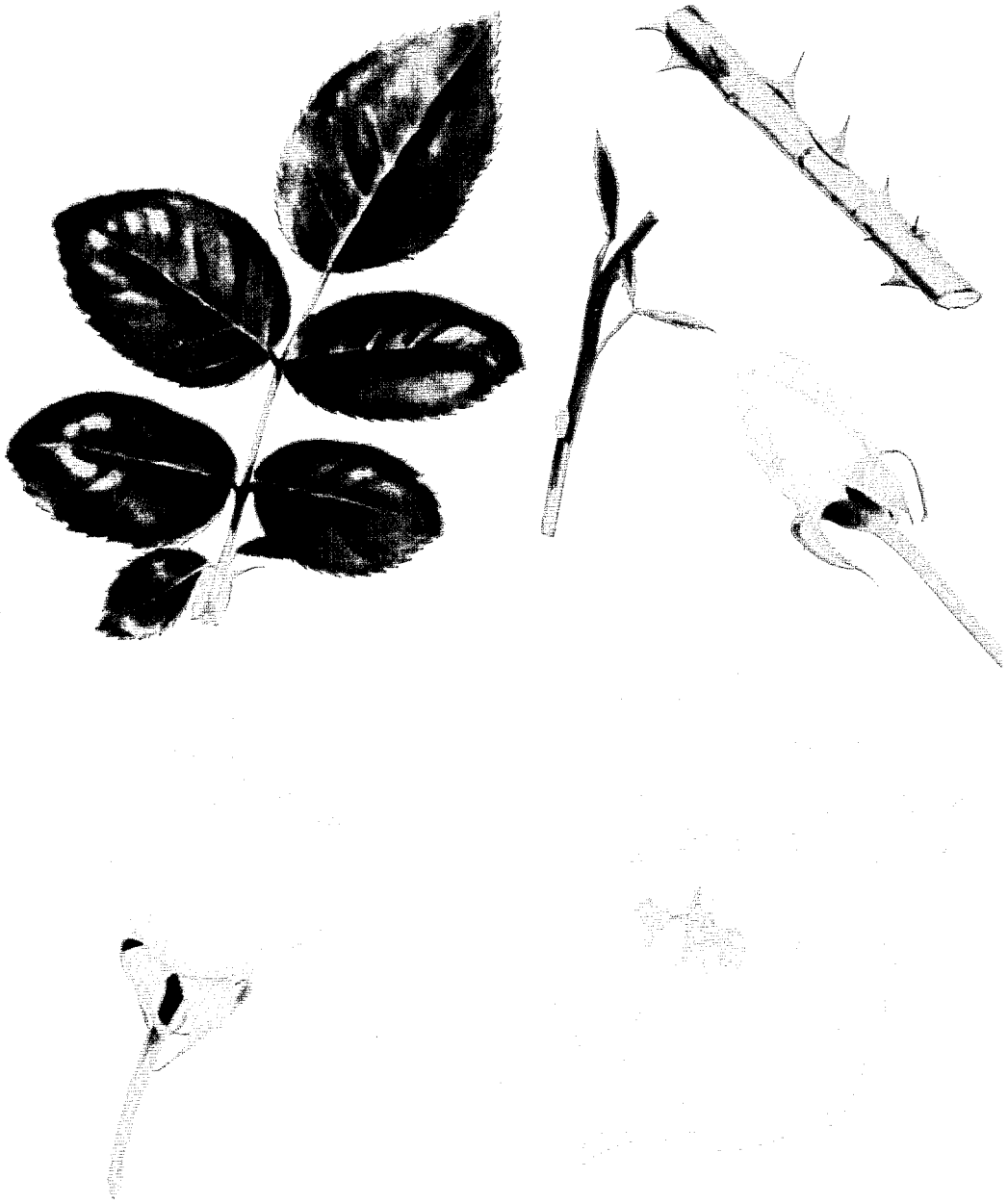
Inventor.
E. S. Boerner
By: Robb & Robb
Attorneys.

United States Patent Office

Plant Pat. 2,729
Patented Mar. 21, 1967

2,729
ROSE PLANT

Eugene S. Boerner, Newark, N.Y., assignor to Jackson & Perkins Company, Newark, N.Y., a corporation of New York Filed Apr. 14, 1966, Ser. No. 542,704
1 Claim. (Cl. Plt.—15)

The present invention relates to a new and distinct variety of rose plant of the hybrid tea class, which was originated by me by crossing two unnamed and unpatented seedlings of the variety known as "Golden Masterpiece" (Plant Patent No. 1,284).

The primary objective of this breeding was to produce a new hybrid tea rose variety which bears large flowers which hold their color and are resistant to sun and wind. This objective was fully achieved, along with other desirable features, as evidenced by the following unique combination of characteristics which are outstanding therein and which distinquish it from its parents, as well as from all other varieties of which I am aware:

(1) A plant habit which attains many breaks and with the foliage extending down to the ground;

(2) Large flowers having an attractive shape;

(3) A very rich and satiny yellow flower color corresponding to Lemon Chrome, lightly overcast with Pale Lemon Chrome; and (4) Long retention of the flower color, with good resistance to sun and wind.

Asexual reproduction of my new variety by budding, as performed at Newark, N.Y., and also at Pleasanton, Calif., shows that the aforementioned characteristics and distinctions come true to form and are established and transmitted through succeeding propagations.

The accompanying drawing shows typical speciments of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—An unnamed seedling of "Golden Masterpiece."
- *Pollen parent.*—Another unnamed seedling of "Golden Masterpiece."

Classification:
- *Botanic.*—Hybrid tea.
- *Comercial.*—Hybrid tea.

*Flower*

(Observations made from specimens grown outdoors at Newark N.Y., in the early morning during the latter part of the month of August.)

Blooming habit: Recurrent—continuous.

Bud:
- *Size.*—Large.
- *Form.*—Ovoid; is not affected by wet or hot weather.
- *Color.*—When sepals first divide—Pale Lemon Yellow, Plate 4, faintly overcast with Nopal Red, Plate 1, over the lower half of the petal. When petals begin to unfurl—Lemon Chrome, Plate 4. When half blown: inside of petals—Pinard Yellow, Plate 4, with lower half of petal overcast with Lemon Chrome, Plate 4; reverse of petals—Lemon Chrome, Plate 4, with lower half of petal overcast with Strontian Yellow, Plate 16.
- *Sepals.*—Serrated; curl back when petals begin to unfurl. Color: inside—Chrysolite Green, Plate 31; outside—Light Cress Green, Plate 31.

- *Calyx.*—Color—Light Cress Green, Plate 31. Shape—Apple. Size—broad. Aspect—smooth. Odor when rubbed—none.
- *Peduncle.* — Length — medium. Aspect — smooth. Strength — erect; slender. Color — Olive Lake, Plate 16.
- *Opening.*—Opens up well; is not affected by adverse weather conditions.

Bloom:
- *Size.*—Large. Average size when fully expanded—5 inches.
- *Borne.*—Both singly and several together.
- *Stems.*—Medium length; strong.
- *Form (when first open).*—High-centered. Permanence—retains its form to the end.
- *Petalage.*—Double (full but open center). Number of petals under normal conditions—from 35 to 40.
- *Color.*—Center of flower—Lemon Chrome, Plate 4. Outer petals—Citron Yellow, Plate 16, very lightly overcast on the outer edge with Lemon Chrome, Plate 4. Base of petals (aiglet)—Lemon Yellow, Plate 4. Inside of petals—Lemon Chrome, Plate 4, lightly overcast with Pale Lemon Chrome, Plate 4. Reverse of petals—Strontian Yellow, Plate 16, with lower half of petal lightly overcast with Lemon Chrome, Plate 4. General tonality from a distance—Lemon Chrome, Plate 4.
- *Discoloration.*—General tonality at end of first day—Lemon Chrome, Plate 4. Second day—Lemon Chrome, Plate 4, lightly overcast with Pale Lemon Chrome, Plate 4. Third day—Lemon Chrome, Plate 4, lightly overcast with Pale Lemon Chrome, Plate 4.

Petals:
- *Texture.*—Thick; is not affected by wet or hot weather.
- *Appearance.*—Inside—satiny. Outside—shiny.
- *Form.*—Oval; slightly notched.
- *Arrangement.*—Imbricated (regularly arranged shingle-like).
- *Petaloids in center.*—Few; small.
- *Persistence.*—Drop off cleanly.
- *Fragrance.*—Moderate. Nature—tea (average hybrid tea scent).
- *Lasting quality.* — On the plant — long. As cut flower—long.

*Genital organs*

Stamens, anthers: Medium size; many; regularly arranged around styles. Color—Buff-Yellow, Plate 4.

Stamens, filaments (threads): Medium length. Color—Lemon Chrome, Plate 4.

Pollen: Color—Maize Yellow, Plate 4.

Styles: Bunched; uneven length; medium length; thin.

Stigmas: Color—Naples Yellow, Plate 16.

Ovaries: All enclosed in calyx.

Hips: None.

Seeds: None.

*Plant*

Form: Bush.

Growth: Vigorous; upright; many breaks and the foliage extending to the ground.

Foilage: Compound of 3 to 7 leaflets.
- *Size.*—Large.
- *Quantity.*—Abundant.
- *Color.* — New foliage: upper side — Dark Cress Green, Plate 31; under side—Yellowish-Oil Green, Plate 5, very lightly overcast with Dresden Brown, Plate 15. Old foliage: upper side—Forest Green, Plate 17; under side—Light Cress Green, Plate 31.
- *Shape.*—Oval.

*Texture.*—Upper side—leathery and glossy. Under side—smooth.

*Ribs and veins.*—Ordinary.

*Edge.*—Serrated (saw toothed).

*Serration.*—Both double and single; small.

*Leaf stem.*—Color—Serpentine Green, Plate 16. Under side—prickly.

*Stipules.*—Medium length; bearded.

Wood:

*New wood.*—Color—Hellebore Green, Plate 17. Bark—smooth.

*Old wood.*—Color—Parrot Green, Plate 6. Bark—smooth.

Thorns:

*Thorns.*—Quantity: on main stalks from base—ordinary; on laterals, from stalks—few. Form—flat base; medium length; some hooked downward and some hooked upward. Color (when young)—Eugenia Red, Plate 13. Position—irregular.

*Prickles.*—Quantity: on main stalk—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a plant habit which attains many breaks and with the foliage extending down to the ground, large flowers having an attractive shape, a very rich and satiny yellow flower color corresponding to Lemon Chrome, lightly overcast with Pale Lemon Chrome and long retention of the flower color, with good resistance to sun and wind.

No references cited.

ABRAHAM G. STONE, *Primary Examiner.*

ROBERT E. BAGWILL, *Assistant Examiner.*